US008859791B2

(12) United States Patent
Li et al.

(10) Patent No.: US 8,859,791 B2
(45) Date of Patent: Oct. 14, 2014

(54) PROCESS FOR PRODUCING AN ALKYLENE OXIDE BY OLEFIN EPOXIDATION

(75) Inventors: Hua Li, Yueyuan (CN); Min Lin, Beijing (CN); Xiaoju Wu, Yueyuan (CN); Wei Wang, Yueyuan (CN); Chijian He, Yueyuan (CN); Jizao Gao, Yueyuan (CN); Xingtian Shu, Beijing (CN); Shuanghua Wan, Yueyuan (CN); Bin Zhu, Beijing (CN)

(73) Assignees: China Petroleum & Chemical Corporation, Beijing (CN); Hunan Changling Petrochemical Science and Technology Development Co. Ltd., Hunan Province (CN); Research Institute of Petroleum Processing, Sinopec, Beijing (CN)

( * ) Notice: Subject to any disclaimer, the term of this patent is extended or adjusted under 35 U.S.C. 154(b) by 0 days.

(21) Appl. No.: 13/878,659

(22) PCT Filed: Oct. 11, 2011

(86) PCT No.: PCT/CN2011/001703
§ 371 (c)(1),
(2), (4) Date: Apr. 17, 2013

(87) PCT Pub. No.: WO2012/048529
PCT Pub. Date: Apr. 19, 2012

(65) Prior Publication Data
US 2013/0211112 A1    Aug. 15, 2013

(30) Foreign Application Priority Data

Oct. 11, 2010   (CN) .......................... 2010 1 0511515
Oct. 11, 2010   (CN) .......................... 2010 1 0511561

(51) Int. Cl.
  *C07D 301/12*   (2006.01)
  *C07D 303/04*   (2006.01)
(52) U.S. Cl.
  CPC ............ *C07D 301/12* (2013.01); *C07D 303/04* (2013.01)
  USPC ...................................................... 549/531
(58) Field of Classification Search
  USPC ................................................ 549/531, 529
  See application file for complete search history.

(56) References Cited

U.S. PATENT DOCUMENTS

| 5,849,937 | A | 12/1998 | Jubin, Jr. et al. | |
| 6,677,467 | B2 * | 1/2004 | Balthasart ................ | 549/531 |
| 2004/0167234 | A1 | 8/2004 | Abazajian et al. | |
| 2004/0176654 | A1 | 9/2004 | Abazajian | |
| 2005/0250955 | A1 * | 11/2005 | Goebbel et al. ............... | 549/529 |
| 2011/0021795 | A1 * | 1/2011 | Kanazawa et al. ............ | 549/518 |

FOREIGN PATENT DOCUMENTS

| CN | 1282328 A | 1/2001 |
| CN | 1449392 A | 10/2003 |
| CN | 1671678 A | 9/2005 |
| CN | 101279959 A | 10/2008 |
| CN | 101314596 A | 12/2008 |

OTHER PUBLICATIONS

International Search Report mailed Jan. 19, 2012, for International Application No. PCT/CN2011/001703.
Extended European Search Report mailed Mar. 27, 2014, for European Application No. 11831926.8, (3 pages).

* cited by examiner

*Primary Examiner* — T. Victor Oh
(74) *Attorney, Agent, or Firm* — Finnegan, Henderson, Farabow, Garrett & Dunner, LLP

(57) ABSTRACT

A process for producing an alkylene oxide by olefin epoxidation, wherein said process comprises the steps of: (1) in a first olefin epoxidation condition, in the presence of a first solid catalyst, a first mixed stream containing a solvent, an olefin and $H_2O_2$ is subjected to an epoxidation in one or more fixed bed reactors and/or one or more moving bed reactors until the conversion of $H_2O_2$ reaches 50%-95%, then, optionally, the resulting reaction mixture obtained in the step (1) is subjected to a separation to obtain a first stream free of $H_2O_2$ and a second stream containing the unreacted $H_2O_2$, and the olefin is introduced to the second stream to produce a second mixed stream, or optionally, the olefin is introduced to the reaction mixture obtained in the step (1) to produce a second mixed stream; (2) in a second olefin epoxidation condition, the reaction mixture obtained in the step (1) or the second mixed stream obtained in the step (1) and a second solid catalyst are introduced to one or more slurry bed reactors to conduct an epoxidation until the total conversion of $H_2O_2$ reaches 98% or more, with a proviso that said process for producing the alkylene oxide by olefin epoxidation has an selectivity for the alkylene oxide of 90% or more.

The process of the present invention combines the slurry bed reactor with the fixed bed reactor and/or the moving bed reactor so as to overcome the disadvantages of the low conversion of $H_2O_2$ in the case that only the fixed bed reactor and/or the moving bed reactor are used, and the low selectivity for the target alkylene oxide in the case that only the slurry bed reactor is used.

9 Claims, No Drawings

PROCESS FOR PRODUCING AN ALKYLENE OXIDE BY OLEFIN EPOXIDATION

TECHNICAL FIELD

The present invention relates to a process for producing an alkylene oxide by olefin epoxidation. In particular, the present invention relates to a process for producing a lower ($C_{2-4}$) alkylene oxide by olefin epoxidation.

BACKGROUND OF THE INVENTION

Currently, the propylene oxide production is mainly conducted worldwide by means of the hydrochlorin route method and the co-oxidation method. The hydrochlorin route method will be gradually eliminated due to the pollution problem. The co-oxidation method seems hardly to be developed to a further large scale due to the limited use of its byproducts. Therefore, the production of propylene oxide is greatly limited by the above production methods. In recent years, a new route for preparing propylene oxide comes out. According to this new route, propylene is epoxidated with an oxidant $H_2O_2$ under the titanium silicate catalysis to become propylene oxide. This route has the advantages such as the mild reaction condition and the environmentally friendly process without pollution, and therefore becomes a new green technology for producing propylene oxide.

CN1671678A discloses an epoxidation method with two fixed bed reactors, wherein the first reactor is an isothermal fixed bed reactor, and the second reactor is a thermal insulation fixed bed reactor. The disadvantage of this method includes the conversion of $H_2O_2$ used in the reaction is not completely, and the unreacted $H_2O_2$ will decompose in the separation column to produce oxygen, which causes a safety concern and even an explosion when badly managed.

CN1449392A discloses a method for preparing an alkylene oxide with a peroxidized compound. In this method, the alkylene oxide is prepared by reacting an olefin and the peroxidized compound in at least two reactors in series (in each of the reactors, a part of catalyst is loaded) in the presence of catalyst and solvent. According to this method, the peroxidized compound is only supplied to the first reactor, and none of the fresh peroxidized compound is added to the subsequent one or more reactors, to each of which the unconsumed peroxidized compound from the preceding reactor is supplied so as to completely convert $H_2O_2$ in the reaction. The reactor used in this method is fixed bed reactor or moving bed reactor. According to this method, at least two reactors are used, preferably three reactors in series. The disadvantages of this method include: if using two reactors at a minimum, the conversion of $H_2O_2$ is still not completely; if using more than two reactors in series, the device cost will increase remarkably and the reaction period of multiple reactors in series is long and the uncontrollable factors in the reaction process are overmuch.

Therefore, there is an urgent need in the prior art to develop a process for producing alkylene oxide by olefin epoxidation, which can completely convert $H_2O_2$ used in the reaction and has a high selectivity for the target alkylene oxide (e.g. propylene oxide).

SUMMARY OF THE INVENTION

The object of the present invention aims at the disadvantages of the lower conversion of $H_2O_2$ and the lower selectivity for the target alkylene oxide (e.g. propylene oxide) in the reaction of the prior art and to provide a process for producing an alkylene oxide by olefin epoxidation, wherein said process has a high conversion of $H_2O_2$ in the reaction and a high selectivity for the obtained target alkylene oxide (e.g. propylene oxide).

In order to accomplish the object of the present invention, the present invention provides a process for producing an alkylene oxide by olefin epoxidation, wherein said process comprises the steps of:

(1) in a first olefin epoxidation condition, in the presence of a first solid catalyst, a first mixed stream containing a solvent, an olefin and $H_2O_2$ is subjected to an epoxidation in one or more fixed bed reactors and/or one or more moving bed reactors until the conversion of $H_2O_2$ reaches 50%-95%, then, optionally, the resulting reaction mixture obtained in the step (1) is subjected to a separation to obtain a first stream free of $H_2O_2$ and a second stream containing the unreacted $H_2O_2$, and the olefin is introduced to the second stream to produce a second mixed stream, or optionally, the olefin is introduced to the reaction mixture obtained in the step (1) to produce a second mixed stream;

(2) in a second olefin epoxidation condition, the reaction mixture obtained in the step (1) or the second mixed stream obtained in the step (1) and a second solid catalyst are introduced to one or more slurry bed reactors to conduct an epoxidation until the total conversion of $H_2O_2$ reaches 98% or more, with a proviso that said process for producing the alkylene oxide by olefin epoxidation has a selectivity for the alkylene oxide (e.g. propylene oxide) of 90% or more.

In one aspect of the process for producing the alkylene oxide by olefin epoxidation according to the present invention, the molar ratio of the solvent, the olefin and $H_2O_2$ is 4-15:0.5-5:1.

In one aspect of the process for producing the alkylene oxide by olefin epoxidation according to the present invention, said solvent is water, acetonitrile, an alcohol having 1-6 carbon atoms, or a mixture thereof.

In one aspect of the process for producing the alkylene oxide by olefin epoxidation according to the present invention, the first olefin epoxidation condition in said fixed bed reactor comprises: the temperature is 30-90° C., the pressure is 0.5-4.5 MPa, the volume space velocity of the first mixed stream is 0.1-7 $h^{-1}$, and the pH is 5-9.5.

In one aspect of the process for producing the alkylene oxide by olefin epoxidation according to the present invention, the first olefin epoxidation condition in said moving bed reactor comprises: the temperature is 30-90° C., the pressure is 0.5-4.5 MPa, the time is 0.2-10 hrs, and the pH is 5-9.5.

In one aspect of the process for producing the alkylene oxide by olefin epoxidation according to the present invention, the second olefin epoxidation condition in said slurry bed reactor comprises: the temperature is 30-90° C., the pressure is 0.5-4.5 MPa, the time is 0.2-10 hrs, and with respect to 100 parts by weight of the reaction mixture obtained in the step (1) or the second mixed stream obtained in the step (1), the used amount of the second solid catalyst is 3-10 parts by weight.

In one aspect of the process for producing the alkylene oxide by olefin epoxidation according to the present invention, said first solid catalyst is a catalyst having a titanium silicate as active component, and said second solid catalyst is a titanium silicate.

In one aspect of the process for producing the alkylene oxide by olefin epoxidation according to the present invention, said process further comprises the reaction mixture obtained in the step (1) is subjected to a separation to obtain a first stream free of $H_2O_2$ and a second stream containing the unreacted $H_2O_2$, and the olefin is introduced to the second stream to obtain a second mixed stream, wherein with respect to 100 parts by weight of the unreacted $H_2O_2$, the amount of the olefin introduced in the second stream is 100-200 parts by weight.

In one aspect of the process for producing the alkylene oxide by olefin epoxidation according to the present invention, the olefin is introduced to the reaction mixture obtained in the step (1) to obtain a second mixed stream, wherein with respect to 100 parts by weight of the unreacted $H_2O_2$ in the reaction mixture obtained in the step (1), 100-200 parts by weight of the olefin is introduced to the reaction mixture obtained in the step (1).

In one aspect of the process for producing the alkylene oxide by olefin epoxidation according to the present invention, said olefin is selected from the group consisting of ethylene, propylene, 1-butene, isobutene, cis-2-butene, trans-2-butene and mixtures thereof.

The process according to the present invention combines at least one slurry bed reactor with at least one fixed bed reactor and/or at least one moving bed reactor so as to overcome the disadvantages of the low conversion of $H_2O_2$ in the case that only the fixed bed reactor and/or the moving bed reactor are used, and the low selectivity for the target alkylene oxide (e.g. propylene oxide) in the case that only the slurry bed reactor is used. In addition, in a preferable embodiment according to the present invention, it is not necessary to use many reactors in series so as to reduce the equipment cost and shorten the product period.

BEST MODE OF CARRYING OUT THE INVENTION

The present invention provides a process for producing an alkylene oxide by olefin epoxidation, wherein said process comprises the steps of:

(1) in a first olefin epoxidation condition, in the presence of a first solid catalyst, a first mixed stream containing a solvent, an olefin and $H_2O_2$ is subjected to an epoxidation in one or more fixed bed reactors and/or one or more moving bed reactors until the conversion of $H_2O_2$ reaches 50%-95%, then, optionally, the resulting reaction mixture obtained in the step (1) is subjected to a separation to obtain a first stream free of $H_2O_2$ and a second stream containing the unreacted $H_2O_2$, and the olefin is introduced to the second stream to produce a second mixed stream, or optionally, the olefin is introduced to the reaction mixture obtained in the step (1) to produce a second mixed stream;

(2) in a second olefin epoxidation condition, the reaction mixture obtained in the step (1) or the second mixed stream obtained in the step (1) and a second solid catalyst are introduced to one or more slurry bed reactors to conduct an epoxidation until the total conversion of $H_2O_2$ reaches 98% or more, with a proviso that said process for producing the alkylene oxide by olefin epoxidation has a selectivity for the alkylene oxide (e.g. propylene oxide) of 90% or more.

The combination of the slurry bed reactor with the fixed bed reactor and/or the moving bed reactor can completely convert $H_2O_2$ used in the reaction, have a very low probability of the side reaction, and remain a relatively high selectivity for the target alkylene oxide (e.g. propylene oxide). In addition, according to the present invention, it is not necessary to use many reactors in series so as to reduce the equipment cost and shorten the product period. According to the present invention, the conversion of $H_2O_2$ in the step (1), the total conversion of $H_2O_2$, and the selectivity for the target alkylene oxide (e.g. propylene oxide) are calculated as follows:

$$\text{Conversion of } H_2O_2 \text{ in the step (1)} = \frac{\text{The mole amount of } H_2O_2 \text{ converted in the step (1)}}{\text{The mole amount of } H_2O_2 \text{ fed in the step (1)}} \times 100\% \quad (I)$$

$$\text{Total conversion of } H_2O_2 = \frac{\text{The total mole amount of the converted } H_2O_2}{\text{The total mole amount of the fed } H_2O_2} \times 100\% \quad (II)$$

$$\text{Selectivity for the target alkylene oxide} = \frac{\text{The mole amount of the produced target alkylene oxide}}{\text{The total mole amount of the produced alkylene oxide}} \times 100\% \quad (III)$$

wherein the mole amount of $H_2O_2$, the mole amount of the target alkylene oxide (e.g. propylene oxide), and the total mole amount of the produced alkylene oxide can be measured by the methods well known to a person skilled in the art. For example, the mole amount of $H_2O_2$ can be measured by the iodometry; and the mole amount of the target alkylene oxide (e.g. propylene oxide) and the total mole amount of the produced alkylene oxide can be measured by the chromatography internal standard method.

According to the present invention, the fixed bed reactor is a reactor widely used in the industry. By the term "fixed bed reactor" is meant a device where the reaction occurs while the fluid flows through the bed formed by the immobile solid materials. In the fixed bed reactor, the catalyst is fixed in the reactor and not mixed with the reactants, and therefore the side reactions are not apt to occur upon using a fixed bed reactor. The selectivity for the target alkylene oxide (e.g. propylene oxide) can be ensured; but the existing problem is the relatively low conversion of $H_2O_2$.

According to the present invention, the moving bed reactor is a reactor which can accomplish the continuous feeding and discharging in a gas-solid phase reaction process or in a liquid-solid phase reaction process. In the moving bed reactor, the back mixing of the reaction materials is little, and therefore the side reactions are not apt to occur upon using a moving bed reactor. The selectivity for the target alkylene oxide (e.g. propylene oxide) can be ensured; but the existing problem is the relatively low conversion of $H_2O_2$.

According to the present invention, the slurry bed reactor is a reactor in which small solid catalyst particles are suspended in the liquid medium. The slurry reactor has a large back-mixing of the reaction materials. After the reaction, the catalyst should generally be separated from the reaction materials so as to be reused. In the slurry bed reactor, the catalyst and the reaction materials are mixed together, and therefore the conversion of $H_2O_2$ is relatively high. However due to the back-mixing, the side reactions are apt to occur, which results in a low yield of the target alkylene oxide (e.g. propylene oxide).

According to the present invention, in said first mixed stream, the contents of the solvent, the olefin and $H_2O_2$ can be varied in a large range. In an embodiment, in said first mixed stream, the molar ratio of the solvent, the olefin and $H_2O_2$ is 4-15:0.5-5:1.

In another embodiment, in said first mixed stream, the molar ratio of the solvent, the olefin and $H_2O_2$ is 4-10:0.5-4:1.

In another embodiment, in said first mixed stream, the molar ratio of the solvent, the olefin and $H_2O_2$ is 4-10:2-4:1.

In another embodiment, in said first mixed stream, the molar ratio of the solvent, the olefin and $H_2O_2$ is 5-8:0.5-1:1.

In another embodiment, in said first mixed stream, the molar ratio of the solvent, the olefin and $H_2O_2$ is 6-8:0.5-0.8:1.

In an embodiment, said first mixed stream can also contain a surfactant. In an embodiment, based on the total weight of said first mixed stream, the content of said surfactant is 0.1-1 wt %. Said surfactant can be an oil-soluble surfactant and/or a water-soluble surfactant, for example, Span 80 and/or Tween 80.

The surfactant is added to the reaction system so as to form an emulsion. Therefore the solubility of the olefin such as propylene in the reaction system increases and the effective availability of the olefin such as propylene increases, which results in that the reaction rate increases; in the meanwhile, the compatibility between the produced target alkylene oxide (e.g. propylene oxide) and the emulsion increases, the diffusion velocity of the target alkylene oxide (e.g. propylene oxide) on the catalyst surface increases, the residual time on the catalyst surface reduces, the side reactions slow down, the reaction selectivity becomes better, and the catalyst life increases.

According to the present invention, the solvents are those well known by a person skilled in the art. In an embodiment, said solvent can be water, acetonitrile, an alcohol having 1-6 carbon atoms, or a mixture thereof. Said alcohol having 1-6 carbon atoms can be methanol, ethanol, propanol and isomers thereof, butanol and isomers thereof, pentanol and isomers thereof. In an embodiment, the solvent is a solvent containing methanol, such as an aqueous methanol solution. In an embodiment, the solvent is methanol.

According to the present invention, the reaction condition in said fixed bed reactor can be varied in a large range. In an embodiment, the reaction condition in said fixed bed reactor includes: the temperature is 30-90° C., the pressure is 0.5-4.5 MPa, the volume space velocity of the first mixed stream is 0.1-7 $h^{-1}$, and the pH is 5-9.5. In another embodiment, the reaction condition in said fixed bed reactor includes: the temperature is 40-80° C., the pressure is 0.6-3 MPa, the volume space velocity of the first mixed stream is 0.4-4 $h^{-1}$, and the pH is 5.5-7. In another embodiment, the reaction condition in said fixed bed reactor includes: the temperature is 35-85° C., the pressure is 1-4 MPa, the volume space velocity of the first mixed stream is 0.5-6 $h^{-1}$, and the pH is 5-7.

According to the present invention, the reaction condition in said moving bed reactor can be varied in a large range. In an embodiment, the reaction condition in said moving bed reactor comprises: the temperature is 30-90° C., the pressure is 0.5-4.5 MPa, the reaction time is 0.2-10 hrs, and the pH is 5-9.5. In another embodiment, the reaction condition in said moving bed reactor comprises: the temperature is 40-80° C., the pressure is 0.6-3 MPa, the reaction time is 1-5 hrs, and the pH is 5.5-7. In another embodiment, the reaction condition in said moving bed reactor comprises: the temperature is 35-85° C., the pressure is 1-4 MPa, the reaction time is 1-8 hrs, and the pH is 5-7.

According to the present invention, the reaction condition in slurry bed reactor can be varied in a large range. In an embodiment, the reaction condition in slurry bed reactor can comprises: the temperature is 30-90° C., the pressure is 0.5-4.5 MPa, the time is 0.2-10 hrs, and with respect to 100 parts by weight of the reaction mixture obtained in the step (1) or the second mixed stream obtained in the step (1), the used amount of the second solid catalyst is 3-10 parts by weight. In another embodiment, the temperature is 40-80° C., the pressure is 0.6-3 MPa, the time is 0.4-4 hrs, and with respect to 100 parts by weight of the reaction mixture obtained in the step (1) or the second mixed stream obtained in the step (1), the used amount of the second solid catalyst is 4-9 parts by weight. In another embodiment, the temperature is 35-85° C., the pressure is 1-4 MPa, the time is 1-8 hrs, and with respect to 100 parts by weight of the reaction mixture obtained in the step (1) or the second mixed stream obtained in the step (1), the used amount of the second solid catalyst is 5-8 parts by weight.

According to the present invention, there is not any specific limitation to the kinds of the first solid catalyst used in the fixed bed reactor and/or the moving bed reactor and the second solid catalyst used in the slurry bed reactor. In an embodiment, said first solid catalyst can be a catalyst having a titanium silicate as active component, and said second solid catalyst can be titanium silicate. If used in a fixed bed reactor, it is necessary to shape the titanium silicate catalyst, so that the shaped catalyst is suitable for the fixed bed reactor. The method of shaping is well known by a person skilled in the art. For example, titanium silicate powder, tetramethoxysilane, silica sol, polyvinyl alcohol, sesbania powder and water can be mixed evenly. The resulting mixture is extruded to shape into particles. The resulting shaped particles are added to an aqueous NaOH solution. The resulting solution is heated to 80-90° C. for 5-10 hrs. After filtering, a solid phase is obtained, washed until neutral, dried and calcined to produce the shaped catalyst that is suitable for the fixed bed reactor. The temperature for drying and calcining can be in a range of 100-600° C. The time for drying and calcining can be in a range of 2-5 hrs.

In an embodiment of the present invention, the present process further comprises: the reaction mixture obtained in the step (1) is subjected to a separation to obtain a first stream free of $H_2O_2$ and a second stream containing the unreacted $H_2O_2$; the olefin is introduced to the second stream to obtain a second mixed stream; and then the second mixed stream is introduced to a slurry bed reactor to conduct the reaction, wherein the first stream free of $H_2O_2$ contains olefin and alkylene oxide such as propylene oxide, and the second stream containing the unreacted $H_2O_2$ further contains solvent and water. Preferably, in the case that the present process further comprises the embodiment in which the reaction mixture obtained in the step (1) is subjected to an separation, in said first mixed stream, the molar ratio of the solvent, the olefin and $H_2O_2$ is 5-8:0.5-1:1. The separation of the reaction mixture obtained in the step (1) can avoid that the breakage in the cyclic structure of the target alkylene oxide (e.g. propylene oxide) obtained in the fixed bed reactor and/or moving bed reactor occurs in the slurry bed reactor. Therefore the generation of by-products decreases and the selectivity for the target alkylene oxide (e.g. propylene oxide) can be further increased. The amount of the introduced olefin can be varied in a large range. In an embodiment, with respect to 100 parts by weight of the unreacted $H_2O_2$, the amount of the olefin introduced in the second stream is 100-200 parts by weight. In another embodiment, with respect to 100 parts by weight of the unreacted $H_2O_2$, the amount of the olefin introduced in the second stream is 100-150 parts by weight.

In an embodiment of the present invention, the present process further comprises: the olefin is introduced to the reaction mixture obtained in the step (1) to obtain a second mixed stream. Preferably, in the case that the present process further comprises the embodiment in which the olefin is introduced to the reaction mixture obtained in the step (1) to obtain a second mixed stream, in said first mixed stream, the molar ratio of the solvent, the olefin and $H_2O_2$ is 5-8:0.5-1:1. The amount of the olefin introduced to the reaction mixture obtained in the step (1) can be varied in a large range. In an embodiment, with respect to 100 parts by weight of the unreacted $H_2O_2$ in the reaction mixture obtained in the step (1), 100-200 parts by weight of the olefin is introduced to the reaction mixture obtained in the step (1). In an embodiment, with respect to 100 parts by weight of the unreacted $H_2O_2$ in the reaction mixture obtained in the step (1), 100-150 parts by weight of the olefin is introduced to the reaction mixture obtained in the step (1).

According to the present invention, the olefin is an olefin having 2-4 carbon atoms, including ethylene, propylene, and butene and isomers thereof. In an embodiment, said olefin is ethylene. In an embodiment, said olefin is propylene. In an embodiment, said olefin is butene, including 1-butene, isobutene, cis-2-butene and trans-2-butene. In a specific embodiment of the present invention, said olefin is propylene.

According to the process of the present invention, in the step (1), one or more fixed bed reactors and/or one or more moving bed reactors can be used.

In an embodiment, the number of the fixed bed reactor is 1, 2, 3, 4, 5 or 6.

In an embodiment, the number of the moving bed reactor is 1, 2, 3, 4, 5 or 6.

In an embodiment, more than one fixed bed reactors can be connected in serial. In an embodiment, more than one fixed bed reactors can be connected in parallel. In an embodiment, more than one fixed bed reactors can be connected in a combination of in series and in parallel.

In an embodiment, more than one moving bed reactors can be connected in serial. In an embodiment, more than one moving bed reactors can be connected in parallel. In an embodiment, more than one moving bed reactors can be connected in a combination of in series and in parallel.

In an embodiment, one or more fixed bed reactors and one or more moving bed reactors can be used in combination. More than one reactors used in combination can be connected in series, in parallel, or in a combination of in series and in parallel.

According to the process of the present invention, in the step (2), one or more slurry bed reactors can be used.

In an embodiment, the number of the slurry bed reactor is 1, 2, 3, 4, 5 or 6.

In an embodiment, more than one slurry bed reactors can be connected in serial. In an embodiment, more than one slurry bed reactors can be connected in parallel. In an embodiment, more than one slurry bed reactors can be connected in a combination of in series and in parallel.

In an embodiment, in the step (1), one fixed bed reactor is used, and in the step (2), one slurry bed reactor is used.

In an embodiment, in the step (1), one moving bed reactor is used, and in the step (2), one slurry bed reactor is used.

In an embodiment, in the step (1), two fixed bed reactors are used in series, and in the step (2), one slurry bed reactor is used.

In an embodiment, in the step (1), two moving bed reactors are used in series, and in the step (2), one slurry bed reactor is used.

In an embodiment, in the step (1), three fixed bed reactor are used in series, and in the step (2), one slurry bed reactor is used.

In an embodiment, in the step (1), three moving bed reactor are used in series, and in the step (2), one slurry bed reactor is used.

Hereinafter, the specific examples are provided to further illustrate the present invention. However, the scope of the present invention is not limited by these examples.

The shaped titanium silicate catalyst, as used in the following examples, was prepared as follows:

100 parts by weight of titanium silicate powder (Hunan Jianchang Petrochemical Co., Ltd. China, HTS) and 10 parts by weight of tetramethoxysilane were mixed evenly. Then to this mixture were added 5 parts by weight of silica sol (having a silica content of 30 wt %), 2 parts by weight of polyvinyl alcohol (commercially available from Sanming Dinghui Chemical Trading Co., Ltd., Model 2099), 1 parts by weight of sesbania powder and 50 parts by weight of water. The resulting mixture was mixed evenly, extruded to shape, and cut into the shaped particles. The shaped particles were then dried at 70° C. for 4 hrs. The resulting shaped bodies had a size of 2 mm×2 mm.

100 g of the above shaped bodies were placed into a 500 mL three-necked flask, to which was added 200 mL of 20 wt % NaOH aqueous solution. The resulting mixture was heated to 90° C. while stirring and kept for 6 hrs. After filtering, a solid phase was obtained, washed with deionized water until neutral, dried at 120° C. for 3 hrs and calcined at 550° C. for 3 hrs to produce the shaped titanium silicate catalyst.

EXAMPLE 1

(1) The above-prepared shaped titanium silicate catalyst was loaded in a fixed bed reactor (purchased from Penglai Luhao Chemical Machinery Co., Ltd.) with a catalyst loading of 15 mL. A first mixed stream containing propylene, methanol and $H_2O_2$ was introduced to the fixed bed reactor, wherein, in said first mixed stream, the molar ratio of methanol, propylene and $H_2O_2$ was 4:4:1. The reaction condition included: the temperature was 35° C., the pressure was 1 MPa, the volume space velocity of the first mixed stream was 0.5 $h^{-1}$, and the pH of the first mixed stream (adjusted with aqueous ammonia) was 5. The amount of $H_2O_2$ in the mixture after the reaction was measured by iodometry, and the conversion of $H_2O_2$ was calculated according to the above equation (I). The result was shown in Table 1. The amount of propylene oxide produced in the step (1) was determined by chromatography internal standard method, and the total amount of alkylene oxide produced in the step (1) was determined by chromatography internal standard method.

(2) The reaction mixture obtained in the step (1) and titanium silicate powder (Hunan Jianchang Petrochemical Co., Ltd., HTS) were introduced with a proportion of 100 parts by weight of the reaction mixture obtained in the step (1) and 5 parts by weight of titanium silicate powder to a slurry bed reactor (purchased from Tianjin Aozhan Technology Co,. Ltd.) to conduct an epoxidation. The reaction temperature was 85° C., the pressure was 4 MPa, and the time was 1 hr. The amount of $H_2O_2$ in the mixture after the reaction was measured by iodometry, the amount of propylene oxide produced in the step (2) was determined by chromatography internal standard method, and the total amount of alkylene oxide produced in the step (2) was determined by chromatography internal standard method. The total conversion of $H_2O_2$ and the selectivity for propylene oxide were calculated according to the above equations (II) and (III). The results were shown in Table 1.

COMPARATIVE EXAMPLE 1

The propylene oxide was prepared in the same manner as Example 1 with the exception that, in the step (2), the reaction mixture obtained in the step (1) was introduced to a fixed bed reactor that was same as that used in the step (1), wherein the catalyst was the above-prepared shaped titanium silicate catalyst and its loading was 15 mL; the reaction condition included: the temperature was 35° C., the pressure was 1 MPa, the volume space velocity was 0.5 $h^{-1}$, and the pH of the mixed stream (adjusted with aqueous ammonia) was 5. The results were shown in Table 1.

COMPARATIVE EXAMPLE 2

The propylene oxide was prepared in the same manner as Example 1 with the exception that, in the step (1), the first mixed stream containing propylene, methanol and $H_2O_2$ was introduced to a slurry bed reactor that was same as that used in the step (2), wherein, in said first mixed stream, the molar ratio of methanol, propylene and $H_2O_2$ was 4:4:1; the weight ratio of said first mixed stream and titanium silicate powder (Hunan Jianchang Petrochemical Co., Ltd., HTS) was 100 parts by weight: 5 parts by weight; the reaction temperature was 85° C.; the pressure was 4 MPa; and the time was 1 hr. The results were shown in Table 1.

EXAMPLE 2

(1) The above-prepared shaped titanium silicate catalyst was loaded in a fixed bed reactor (purchased from Penglai Luhao Chemical Machinery Co., Ltd.) with a catalyst loading of 15 mL. A first mixed stream containing propylene, methanol and $H_2O_2$ was introduced to the fixed bed reactor, wherein, in said first mixed stream, the molar ratio of methanol, propylene and $H_2O_2$ was 10:3:1. The reaction condition included: the reaction temperature was 75° C., the reaction pressure was 4 MPa, the volume space velocity of the first mixed stream was 6 $h^{-1}$, and the pH of the first mixed stream (adjusted with aqueous ammonia) was 9.5. The amount of $H_2O_2$ in the mixture after the reaction was measured by iodometry, and the conversion of $H_2O_2$ was calculated according to the above equation (I). The result was shown in Table 1. The amount of propylene oxide produced in the step (1) was determined by chromatography internal standard method, and the total amount of alkylene oxide produced in the step (1) was determined by chromatography internal standard method.

(2) The reaction mixture obtained in the step (1) and titanium silicate powder (Hunan Jianchang Petrochemical Co., Ltd., HTS) were introduced with a proportion of 100 parts by weight of the reaction mixture obtained in the step (1) and 8 parts by weight of titanium silicate powder to a slurry bed reactor (purchased from Tianjin Aozhan Technology Co,. Ltd.) to conduct an epoxidation. The reaction temperature was 40° C.; the reaction pressure was 1.5 MPa; and the reaction time was 8 hrs. The amount of $H_2O_2$ in the mixture after the reaction was measured by iodometry, the amount of propylene oxide produced in the step (2) was determined by chromatography internal standard method, and the total amount of alkylene oxide produced in the step (2) was determined by chromatography internal standard method. The total conversion of $H_2O_2$ and the selectivity for propylene oxide were calculated according to the above equations (II) and (III). The results were shown in Table 1.

EXAMPLE 3

(1) The above-prepared shaped titanium silicate catalyst was loaded in a fixed bed reactor (purchased from Penglai Luhao Chemical Machinery Co., Ltd.) with a catalyst loading of 15 mL. A first mixed stream containing propylene, methanol and $H_2O_2$ was introduced to the fixed bed reactor, wherein, in said first mixed stream, the molar ratio of methanol, propylene and $H_2O_2$ was 8:0.8:1. The reaction condition included: the reaction temperature was 50° C., the reaction pressure was 3 MPa, the volume space velocity of the first mixed stream is 5 $h^{-1}$, and the pH of the first mixed stream (adjusted with aqueous ammonia) was 6. The amount of $H_2O_2$ in the mixture after the reaction was measured by iodometry, and the conversion of $H_2O_2$ was calculated according to the above equation (I). The result was shown in Table 1. The amount of propylene oxide produced in the step (1) was determined by chromatography internal standard method, and the total amount of alkylene oxide produced in the step (1) was determined by chromatography internal standard method.

(2) The reaction mixture obtained in the step (1) was introduced into a $H_2O_2$ separation column to be subjected to a separation to obtain a first stream free of $H_2O_2$ and a second stream containing the unreacted $H_2O_2$. The content of the unreacted $H_2O_2$ in the second stream was measured by iodometry.

(3) The second stream (in which propylene was added) and titanium silicate powder (Hunan Jianchang Petrochemical Co., Ltd., HTS) were introduced with a proportion of 100 parts by weight of the second stream (in the second stream, with respect to 100 parts by weight of the unreacted $H_2O_2$, was added 150 parts by weight of propylene) and 5 parts by weight of titanium silicate powder to a slurry bed reactor (purchased from Tianjin Aozhan Technology Co,. Ltd.) to conduct an epoxidation. The reaction stream was adjusted with aqueous ammonia to pH=6. The reaction temperature was 45° C.; the reaction pressure was 2 MPa, and the reaction time was 3 hrs. The amount of $H_2O_2$ in the mixture after the reaction was measured by iodometry, the amount of propylene oxide produced in the step (3) was determined by chromatography internal standard method, and the total amount of alkylene oxide produced in the step (3) was determined by chromatography internal standard method. The total conversion of $H_2O_2$ and the selectivity for propylene oxide were calculated according to the above equations (II) and (III). The results were shown in Table 1.

EXAMPLE 4

(1) The above-prepared shaped titanium silicate catalyst was loaded in a fixed bed reactor (purchased from Penglai Luhao Chemical Machinery Co., Ltd.) with a catalyst loading of 15 mL. A first mixed stream containing propylene, methanol and $H_2O_2$ was introduced to the fixed bed reactor, wherein, in said first mixed stream, the molar ratio of methanol, propylene and $H_2O_2$ was 6:1:1. The reaction condition included: the reaction temperature was 40° C., the reaction pressure was 2.5 MPa, the volume space velocity of the first mixed stream was 2 $h^{-1}$, and the pH of the first mixed stream (adjusted with aqueous ammonia) was 6. The amount of $H_2O_2$ in the mixture after the reaction was measured by iodometry, and the conversion of $H_2O_2$ was calculated according to the above equation (I). The result was shown in Table 1. The amount of propylene oxide produced in the step (1) was determined by chromatography internal standard method, and the total amount of alkylene oxide produced in the step (1) was determined by chromatography internal standard method.

(2) The above reaction mixture (in which propylene was added) and titanium silicate powder (Hunan Jianchang Petrochemical Co., Ltd., HTS) were introduced with a proportion of 100 parts by weight of the reaction mixture obtained in the step (1) (in the reaction mixture, with respect to 100 parts by weight of the unreacted $H_2O_2$, was added 100 parts by weight of propylene) and 6 parts by weight of titanium silicate powder to a slurry bed reactor (purchased from Tianjin Aozhan Technology Co,. Ltd.) to conduct an epoxidation. The reaction temperature was 55° C.; the reaction pressure was 2.3 MPa; and the reaction time was 5.5 hrs. The amount of $H_2O_2$ in the mixture after the reaction was measured by iodometry, the amount of propylene oxide produced in the step (2) was determined by chromatography internal standard method, and the total amount of alkylene oxide produced in the step (2) was determined by chromatography internal standard method.

The total conversion of $H_2O_2$ and the selectivity for propylene oxide were calculated according to the above equations (II) and (III). The results were shown in Table 1.

TABLE 1

| No. | Conversion of $H_2O_2$ in the step (1) | Total conversion of $H_2O_2$ | Selectivity for propylene oxide |
|---|---|---|---|
| Example 1 | 50.1% | 98.5% | 95.6% |
| Comparative Example 1 | 50.1% | 90.2% | 99.0% |
| Comparative Example 2 | 87% | 99.7% | 87.2% |
| Example 2 | 78% | 98.4% | 96.2% |
| Example 3 | 60% | 99.5% | 99.1% |
| Example 4 | 70% | 98.2% | 95.4% |

It was seen from the data in Table 1 that the combination of the fixed bed reactor and the slurry bed reactor could increase the total conversion of $H_2O_2$, reduce the possibility of the side-reactions, and have a relatively high selectivity for propylene oxide. It was seen from the comparison of Example 1 with Comparative Examples 1-2 that the combination of the fixed bed reactor and the slurry bed reactor could overcome the disadvantages of the low conversion of $H_2O_2$ in the case that only the fixed bed reactor was used, and the low selectivity for propylene oxide in the case that only the slurry bed reactor was used. In addition, it was not necessary to use many reactors in series so as to reduce the equipment cost.

EXAMPLE 5

(1) Titanium silicate powder (Hunan Jianchang Petrochemical Co., Ltd., HTS) catalyst was loaded in a moving bed reactor (purchased from Chengdu YonTon Machinery Factory). A first mixed stream containing propylene, methanol and $H_2O_2$ was introduced to the moving bed reactor, wherein, in said first mixed stream, the molar ratio of methanol, propylene and $H_2O_2$ was 10:4:1, and the catalyst concentration in said first mixed stream was 5 wt %. The reaction condition included: the temperature was 35° C., the pressure was 1 MPa, the time was 8 hrs, and the pH of the first mixed stream (adjusted with aqueous ammonia) was 5. The amount of $H_2O_2$ in the mixture after the reaction was measured by iodometry, and the conversion of $H_2O_2$ was calculated according to the above equation (I). The result was shown in Table 2. The amount of propylene oxide produced in the step (1) was determined by chromatography internal standard method, and the total amount of alkylene oxide produced in the step (1) was determined by chromatography internal standard method.

(2) The reaction mixture obtained in the step (1) and titanium silicate powder (Hunan Jianchang Petrochemical Co., Ltd., HTS) were introduced with a proportion of 100 parts by weight of the reaction mixture obtained in the step (1) and 5 parts by weight of titanium silicate powder to a slurry bed reactor (purchased from Tianjin Aozhan Technology Co,. Ltd.) to conduct an epoxidation. The reaction temperature was 85° C., the pressure was 4 MPa, and the time was 1 hr. The amount of $H_2O_2$ in the mixture after the reaction was measured by iodometry, the amount of propylene oxide produced in the step (2) was determined by chromatography internal standard method, and the total amount of alkylene oxide produced in the step (2) was determined by chromatography internal standard method. The total conversion of $H_2O_2$ and the selectivity for propylene oxide were calculated according to the above equations (II) and (III). The results were shown in Table 2.

COMPARATIVE EXAMPLE 3

The propylene oxide was prepared in the same manner as Example 5 with the exception that, in the step (2), the reaction mixture obtained in the step (1) was introduced to a moving bed reactor that was same as that used in the step (1), wherein the catalyst concentration in the reaction mixture was 5 wt %; the reaction condition included: the temperature was 35° C., the pressure was 1 MPa, the reaction time was 2 hrs, and the pH of the mixed stream (adjusted with aqueous ammonia) was 5. The results were shown in Table 2.

COMPARATIVE EXAMPLE 4

The propylene oxide was prepared in the same manner as Example 5 with the exception that, in the step (1), the first mixed stream containing propylene, methanol and $H_2O_2$ was introduced to a slurry bed reactor that was same as that used in the step (2), wherein, in said first mixed stream, the molar ratio of methanol, propylene and $H_2O_2$ was 10:4:1; the catalyst concentration in said first mixed stream was 5 wt %; the reaction temperature was 85° C.; the pressure was 4 MPa; and the time was 1 hr. The results were shown in Table 2.

EXAMPLE 6

(1) Titanium silicate powder (Hunan Jianchang Petrochemical Co., Ltd., HTS) catalyst was loaded in a moving bed reactor (purchased from Chengdu YonTon Machinery Factory). A first mixed stream containing propylene, methanol, and $H_2O_2$ was introduced to the moving bed reactor, wherein, in said first mixed stream, the molar ratio of methanol, propylene and $H_2O_2$ was 4:2:1, and the catalyst concentration in said first mixed stream was 5 wt %. The reaction condition included: the reaction temperature was 75° C., the reaction pressure was 4 MPa, the time was 2 hrs, and the pH of the first mixed stream (adjusted with aqueous ammonia) was 9.5. The amount of $H_2O_2$ in the mixture after the reaction was measured by iodometry, and the conversion of $H_2O_2$ was calculated according to the above equation (I). The result was shown in Table 2. The amount of propylene oxide produced in the step (1) was determined by chromatography internal standard method, and the total amount of alkylene oxide produced in the step (1) was determined by chromatography internal standard method.

(2) The reaction mixture obtained in the step (1) and titanium silicate powder (Hunan Jianchang Petrochemical Co., Ltd., HTS) were introduced with a proportion of 100 parts by weight of the reaction mixture obtained in the step (1) and 8 parts by weight of titanium silicate powder to a slurry bed reactor (purchased from Tianjin Aozhan Technology Co,. Ltd.) to conduct an epoxidation. The reaction temperature was 40° C., the reaction pressure was 1.5 MPa, and the reaction time was 8 hrs. The amount of $H_2O_2$ in the mixture after the reaction was measured by iodometry, the amount of propylene oxide produced in the step (2) was determined by chromatography internal standard method, and the total amount of alkylene oxide produced in the step (2) was determined by chromatography internal standard method. The total conversion of $H_2O_2$ and the selectivity for propylene oxide were calculated according to the above equations (II) and (III). The results were shown in Table 2.

EXAMPLE 7

(1) Titanium silicate powder (Hunan Jianchang Petrochemical Co., Ltd., HTS) catalyst was loaded in a moving bed reactor (purchased from Chengdu YonTon Machinery Factory). A first mixed stream containing propylene, methanol and $H_2O_2$ was introduced to the moving bed reactor, wherein, in said first mixed stream, the molar ratio of methanol, propylene and $H_2O_2$ was 6:0.5:1, and the catalyst concentration in said first mixed stream was 5 wt %. The reaction condition included: the reaction temperature was 50° C., the reaction pressure was 3 MPa, the time was 5 hrs, and the pH of the first mixed stream (adjusted with aqueous ammonia) was 6. The amount of $H_2O_2$ in the mixture after the reaction was measured by iodometry, and the conversion of $H_2O_2$ was calculated according to the above equation (I). The result was shown in Table 2. The amount of propylene oxide produced in the step (1) was determined by chromatography internal standard method, and the total amount of alkylene oxide produced in the step (1) was determined by chromatography internal standard method.

(2) The reaction mixture obtained in the step (1) was introduced into a $H_2O_2$ separation column to be subjected to a separation to obtain a first stream free of $H_2O_2$ and a second stream containing the unreacted $H_2O_2$. The content of the unreacted $H_2O_2$ in the second stream was measured by iodometry.

(3) The second stream (in which propylene was added) and titanium silicate powder (Hunan Jianchang Petrochemical Co., Ltd., HTS) were introduced with a proportion of 100 parts by weight of the second stream (in the second stream, with respect to 100 parts by weight of the unreacted $H_2O_2$, was added 150 parts by weight of propylene) and 5 parts by weight of titanium silicate powder to a slurry bed reactor (purchased from Tianjin Aozhan Technology Co,. Ltd.) to conduct an epoxidation. The reaction stream was adjusted with aqueous ammonia to pH=9.5. The reaction temperature was 45° C., the reaction pressure was 2 MPa, and the reaction time was 3 hrs. The amount of $H_2O_2$ in the mixture after the reaction was measured by iodometry, the amount of propylene oxide produced in the step (3) was determined by chromatography internal standard method, and the total amount of alkylene oxide produced in the step (3) was determined by chromatography internal standard method. The total conversion of $H_2O_2$ and the selectivity for propylene oxide were calculated according to the above equations (II) and (III). The results were shown in Table 2.

EXAMPLE 8

(1) Titanium silicate powder (Hunan Jianchang Petrochemical Co., Ltd., HTS) catalyst was loaded in a moving bed reactor (purchased from Chengdu YonTon Machinery Factory). A first mixed stream containing propylene, methanol and $H_2O_2$ was introduced to the moving bed reactor, wherein, in said first mixed stream, the molar ratio of methanol, propylene and $H_2O_2$ was 5:1:1, and the catalyst concentration in said first mixed stream was 5 wt %. The reaction condition included: the reaction temperature was 40° C., the reaction pressure was 2.5 MPa, the time was 5.5 hrs, and the pH of the first mixed stream (adjusted with aqueous ammonia) was 6. The amount of $H_2O_2$ in the mixture after the reaction was measured by iodometry, and the conversion of $H_2O_2$ was calculated according to the above equation (I). The result was shown in Table 2. The amount of propylene oxide produced in the step (1) was determined by chromatography internal standard method, and the total amount of alkylene oxide produced in the step (1) was determined by chromatography internal standard method.

(2) The reaction mixture obtained in the step (1) (in which propylene was added) and titanium silicate powder were introduced with a proportion of 100 parts by weight of the reaction mixture obtained in the step (1) (in the reaction mixture, with respect to 100 parts by weight of the unreacted $H_2O_2$, was added 100 parts by weight of propylene) and 6 parts by weight of titanium silicate powder (Hunan Jianchang Petrochemical Co., Ltd., HTS) to a slurry bed reactor (purchased from Tianjin Aozhan Technology Co,. Ltd.) to conduct an epoxidation. The reaction temperature was 55° C.; the reaction pressure was 2.3 MPa; the reaction time was 5.5 hrs. The amount of $H_2O_2$ in the mixture after the reaction was measured by iodometry, the amount of propylene oxide produced in the step (2) was determined by chromatography internal standard method, and the total amount of alkylene oxide produced in the step (2) was determined by chromatography internal standard method. The total conversion of $H_2O_2$ and the selectivity for propylene oxide were calculated according to the above equations (II) and (III). The results were shown in Table 2.

TABLE 2

| No. | Conversion of $H_2O_2$ in the step (1) | Total conversion of $H_2O_2$ | Selectivity for propylene oxide |
|---|---|---|---|
| Example 5 | 50.5% | 98.2% | 95.3% |
| Comparative Example 3 | 50.5% | 89.9% | 98.7% |
| Comparative Example 4 | 87.5% | 99.4% | 86.7% |
| Example 6 | 78.6% | 98.1% | 96.0% |
| Example 7 | 60.3% | 99.2% | 98.8% |
| Example 8 | 70.5% | 97.9% | 95.1% |

It was seen from the data in Table 2 that the combination of the moving bed reactor and the slurry bed reactor could increase the total conversion of $H_2O_2$, reduce the possibility of the side-reactions, and have a relatively high selectivity for propylene oxide.

It was seen from the comparison of Example 5 with Comparative Examples 3-4 that the combination of the moving bed reactor and the slurry bed reactor could overcome the disadvantages of the low conversion of $H_2O_2$ in the case that only the moving bed reactor was used, and the low selectivity for propylene oxide in the case that only the slurry bed reactor was used. In addition, it was not necessary to use many reactors in series so as to reduce the equipment cost.

In summary, the process according to the present invention combines at least one slurry bed reactor with at least one fixed bed reactor and/or at least one moving bed reactor so as to overcome the disadvantages of the low conversion of $H_2O_2$ in the case that only the fixed bed reactor and/or the moving bed reactor are used, and the low selectivity for the target alkylene oxide in the case that only the slurry bed reactor is used. In addition, according to the present invention, it is not necessary to use many reactors in series so as to reduce the equipment cost and shorten the product period.

The invention claimed is:

1. A process for producing an alkylene oxide by olefin epoxidation, wherein said process comprises the steps of:
    (1) in a first olefin epoxidation condition, in the presence of a first solid catalyst, a first mixed stream containing a solvent, an olefin and $H_2O_2$ is subjected to an epoxidation in one or more fixed bed reactors and/or one or more moving bed reactors until the conversion of $H_2O_2$ reaches 50%-95%, then, optionally, the resulting reaction mixture obtained in the step (1) is subjected to a separation to obtain a first stream free of $H_2O_2$ and a second stream containing the unreacted $H_2O_2$, and the olefin is introduced to the second stream to produce a second mixed stream, or optionally, the olefin is introduced to the reaction mixture obtained in the step (1) to produce a second mixed stream;

(2) in a second olefin epoxidation condition, the reaction mixture obtained in the step (1) or the second mixed stream obtained in the step (1) and a second solid catalyst are introduced to one or more slurry bed reactors to conduct an epoxidation until the total conversion of $H_2O_2$ reaches 98% or more, with a proviso that said process for producing the alkylene oxide by olefin epoxidation has an selectivity for the alkylene oxide of 90% or more, Further wherein said first solid catalyst is a catalyst having a titanium silicate as active component, and said second solid catalyst is a titanium silicate.

2. The process according to claim 1, wherein the molar ratio of the solvent, the olefin and $H_2O_2$ is 4-15:0.5-5:1.

3. The process according to claim 1, wherein said solvent is water, acetonitrile, an alcohol having 1-6 carbon atoms, or a mixture thereof.

4. The process according to claim 1, wherein the first olefin epoxidation condition in said fixed bed reactor comprises: the temperature is 30-90° C., the pressure is 0.5-4.5 MPa, the volume space velocity of the first mixed stream is 0.1-7 h$^{-1}$ and the pH is 5-9.5.

5. The process according to claim 1, wherein the first olefin epoxidation condition in said moving bed reactor comprises: the temperature is 30-90° C., the pressure is 0.5-4.5 MPa, the time is 0.2-10 hrs, and the pH is 5-9.5.

6. The process according to claim 1, wherein the second olefin epoxidation condition in said slurry bed reactor comprises: the temperature is 30-90°, the pressure is 0.5-4.5 MPa, the time is 0.2-10 hrs, and with respect to 100 parts by weight of the reaction mixture obtained in the step (1) or the second mixed stream obtained in the step (1), the used amount of the second solid catalyst is 3-10 parts by weight.

7. The process according to claim 1, wherein said process further comprises the reaction mixture obtained in the step (1) is subjected to a separation to obtain a first stream free of $H_2O_2$ and a second stream containing the unreacted $H_2O_2$, and the olefin is introduced to the second stream to obtain a second mixed stream, wherein with respect to 100 parts by weight of the unreacted $H_2O_2$, the amount of the olefin introduced in the second stream is 100-200 parts by weight.

8. The process according to claim 1, wherein said process further comprises the olefin is introduced to the reaction mixture obtained in the step (1) to obtain a second mixed stream, wherein with respect to 100 parts by weight of the unreacted $H_2O_2$ in the reaction mixture obtained in the step (1), 100-200 parts by weight of the olefin is introduced to the reaction mixture obtained in the step (1).

9. The process according to claim 1, wherein said olefin is selected from the group consisting of ethylene, propylene, 1-butene, isobutene, cis-2-butene, trans-2-butene and mixtures thereof.

* * * * *